United States Patent [19]

Tanaka et al.

[11] Patent Number: 5,801,221
[45] Date of Patent: Sep. 1, 1998

[54] POLYMERIC PHASE TRANSITION ARTIFICIAL RECEPTORS, ANTIBODIES, AND ENZYMES

[75] Inventors: Toyoichi Tanaka, Wellesley, Mass.; Masahiko Annaka, Yokohama, Japan; Saturo Masamune, Newton, Mass.

[73] Assignee: Massachusetts Institute of Technology, Cambridge, Mass.

[21] Appl. No.: 460,385

[22] Filed: Jun. 2, 1995

Related U.S. Application Data

[63] Continuation of Ser. No. 155,001, Nov. 19, 1993, abandoned, which is a continuation-in-part of Ser. No. 62,134, May 17, 1993, abandoned.

[51] Int. Cl.$^6$ ............................................. C08F 271/00
[52] U.S. Cl. ............ 525/328.4; 525/244; 525/259; 525/328.3; 525/359.6; 525/377; 526/292.95; 526/204; 526/205; 526/215; 526/216
[58] Field of Search ........................ 210/635, 656, 210/198.2; 526/292.95, 204, 205, 215, 216; 525/244, 259, 328.3, 328.4, 359.6, 377; 521/99, 128

[56] References Cited

U.S. PATENT DOCUMENTS

| | | |
|---|---|---|
| 3,788,950 | 1/1974 | Hicks et al. . |
| 3,859,169 | 1/1975 | O'Driscoll et al. . |
| 4,012,570 | 3/1977 | Dean et al. . |
| 4,411,754 | 10/1983 | Kaetsu et al. . |
| 4,421,855 | 12/1983 | Watanabe et al. . |
| 4,524,137 | 6/1985 | Hägerdal et al. . |
| 4,737,544 | 4/1988 | McCain et al. . |
| 5,110,833 | 5/1992 | Mosbach ................................. 521/50 |
| 5,242,491 | 9/1993 | Mamada et al. . |

OTHER PUBLICATIONS

Annaka et al., "Multiple Phases of Polymer Gels", Nature, vol. 355, pp. 430–432, Jan. 1992.

H S Chan et al. (1993) Physics Today 46, 24–32 "the Protein Folding Problem".

A. Rich (1977) Accounts Chem Res. 10, 388–396 "The-Dimensional Structure and Biological Function of Transfer RNA."

*Primary Examiner*—Mark Nagumo
*Attorney, Agent, or Firm*—Choate, Hall & Stewart; Sam Pasternack; Mary Rose Scozzafava

[57] ABSTRACT

Multiple-phase transition copolymers are formed which can selectively bind and release a chemical, or which can selectively catalyze a specific chemical reaction.

16 Claims, 3 Drawing Sheets

POLYMERIC PHASE TRANSITION ARTIFICIAL RECEPTORS, ANTIBODIES, AND ENZYMES

RELATED APPLICATION

This is a continuation of appliation Ser. No. 08/155,001 filed on Nov. 19, 1993, abandoned, which is a continuation-in-part of U.S. Ser. No. 08/062,134 filed May 17, 1993, now abandoned.

GOVERNMENT SUPPORT

Support for at least some of the work described and claimed herein was provided under the terms of Contract No. DMR-9022933, awarded by the National Science Foundation. Therefore, the Government has certain rights to subject matter claimed herein.

BACKGROUND OF THE INVENTION

Receptors, antibodies, and enzymes have a common ability to selectively bind molecules. However, known receptors, antibodies, and enzymes have only a limited capacity for manipulation to control binding and, possibly, release of the molecules or products formed from the bound molecules.

Therefore, a need exists for artificial receptors, antibodies, and enzymes which overcome or minimize the above-mentioned problems.

SUMMARY OF THE INVENTION

1. Proteins: Polymers with Structure and Function

Proteins are linear chain molecules in which twenty kinds of amino acids are connected in specific sequences. They can fold into unique structures and perform various sophisticated functions and serve as molecular receptors to receive molecular messages, antibodies to recognize alien molecules and cells, and enzymes that catalyze biochemical reactions. They are the key molecules to maintain life. General principles are not known, however, with which to design and synthesize such polymers that can form structures and function like proteins. The current biotechnology depends on the biological systems and biological information as given in the DNA sequences obtained from biological cells.

If such general principles are known, it will be possible to design and synthesize polymers that will have functions similar to proteins. More specifically, polymers may be synthesized that can specifically bind target molecules and release them upon their conformational changes, or polymers that can catalyze chemical reactions.

2. Theories on Unique Structure of Heteropolymers

The sequence of amino acids was considered to be essential for the protein to have a particular structure and exercise specific functions. Recent theoretical studies have shown, however, that for a polymer to fold into a unique structure the polymer does not have to have a specific sequence, but the composition of the monomers that construct the polymer has to satisfy a compositional requirement (Shachnovich & Gutin (1989)). The requirement for a composition is practically infinitely easier than the requirement of a sequence. Of course, the structures are usually different for different sequences, but whether or not a polymer can fold into a unique, thermodynamically stable structure depends only on the composition of the constituent monomers.

For a polymer to have a molecular recognition capability, structural requirement is imposed only on the active site area where monomers should be arranged in such a way that they fit perfectly to the target molecule. The other portion of the polymer must have a stable structure, but the structure can be any one. Therefore, except for the active site, polymers can be made by using a proper composition of monomers without specifying the sequence. As we shall see later, the active site configuration can be created by methods of molecular imprinting.

3. Discovery of Multiple Phases of Heteropolymer Gels

Until now no synthetic polymers were known to have such a stable state, similar to that of proteins. We have recently discovered that a synthetic polymer can have stable phases with possibly discrete structures, and undergo discontinuous phase transition between these stable phases (Annaka & Tanaka (1992)). A necessary condition is that the polymer be made of random copolymers whose segments are interacting with repulsive as well as attractive forces. The attractions have to be a combination of hydrogen bonding and one or more of the other fundamental biological interactions, such as van der Waals, hydrophobic, and electrostatic (between plus and minus charges) interactions (Tanaka and Annaka (1993)). A proper composition of these forces is required for the achievement of the new phases.

4. Method of Molecular Imprinting

Another important development is the method of molecular imprinting to create polymers that are capable of recognizing target molecules (Wulff, Mosbach, Shea). In these methods, highly crosslinked plastics are formed in the presence of target molecules. When the target molecules are washed away, there remain holes that fit to the target molecules. In this case the stability is obtained by high cross-linking density rather than by the cooperative monomer-monomer interactions as in the case of proteins.

Based on these findings we have devised a generic method to synthesize copolymers that are capable of molecular recognition (artificial antibodies) or catalytic activities (artificial enzymes).

Artificial Antibodies

The present invention relates to a method of forming a multiple-phase transition copolymer which can selectively bind a substrate, and release the substrate upon undergoing volume phase transition. The invention also relates to multiple-phase transition copolymers which are formed by the method of invention. Such polymers will have specific molecular recognition, absorption and recovery of the substrate.

In one embodiment, the method includes forming a monomer solution, which, upon polymerization, will form a copolymer gel which exhibits multiple-phase transition at a plurality of phase transition conditions. Prior to polymerization the template molecules, which are the substrate or substrate analogues, are added to the solution. The combined monomer solution and template are exposed to conditions sufficient to cause the monomer solution to polymerize and form the copolymer. The copolymer is then brought to an expanding phase transition by varying temperature, solvent or other parameters, so that the templates are washed away from the copolymers. The copolymers are then exposed to a change in environmental conditions, such as temperature or solvent, to return to the original stable state. Such copolymers will show the specific binding of the substrate molecules.

Artificial Enzymes

The present invention relates to a method of forming a multiple-phase transition copolymer which can selectively catalyze a substrate, and release the product(s) upon undergoing volume phase transition. The invention also relates to multiple-phase transition copolymers which are formed by the method of invention. Such polymers will have specific catalytic activity upon a substrate and recovery of the products into which the substrate is converted.

In one embodiment, the method includes forming a monomer solution which, upon polymerization, will form a copolymer gel which exhibits multiple-phase transition at a plurality of phase transition conditions. Prior to polymerization the template molecules mimicking the substrate in its transition state are added to the solution. Enzymes are known to recognize its substrate in its transition state into the products. Such mimicking molecules have been developed for various substrates. The combined monomer solution and template are exposed to conditions sufficient to cause the monomer solution to polymerize and form the copolymer. The copolymer is then brought to an expanding phase transition by varying temperature, solvent and other parameters, so that the templates are washed away from the copolymers. The copolymers are then exposed to a change in environmental conditions, such as temperature or solvent, to return to the original stable state. Such polymers will have specific catalytic activity upon a substrate and recovery of the products into which the substrate is converted.

The advantage of this invention includes formation of phase transition copolymers which can selectively bind a substrate or can carry out selective catalytic conversion of a substrate into products. The copolymers can be manipulated through phase transitions to absorb substrates and release substrates or products which are formed during conversion of the substrates. The copolymers, thus formed, will be able to mimic the operation of chemical receptors, antibodies, and enzymes.

DETAILED DESCRIPTION OF THE INVENTION

The features and other details of the phase-transition copolymers and methods of forming the phase-transition copolymers will now be more particularly described and pointed out in the claims. It will be understood that the particular embodiments of the invention are shown by way of illustration and not as limitations of the invention. The principle features of this invention can be employed in various embodiments without departing from the scope of the invention.

"Phase-transition" of gels, as that term is used herein, means a discontinuous volume change of gels between an expanded phase and a more contracted phase or vice-versa. "Phase-transition gels," as that term is used herein, are gels which exhibit a phase transition at a phase-transition condition. The difference in volume between the expanded and the contracted phase of the phase-transition gels can be as large as many thousands of times. Examples of phase-transition gels are disclosed in Tanaka et al., U.S. Pat. No. 4,732,930 and U.S. Pat. No. 5,242,491 and 5,100,933, the teachings of which are incorporated herein by reference.

"Multiple-phase transition gels," as that term is used herein, means gels which can exhibit phase transitions at a plurality of distinct phase-transition conditions. For example, a multiple-phase transition gel or copolymer could exhibit an expanding phase transition by lowering the temperature of the gel at a first temperature and, after the first expanding phase transition and continued lowering of temperature, exhibit a second expanding phase transition at a lower temperature than that at which the first expanding phase transition occurred.

Examples of multiple-phase transition gels are described in Annaka and Tanaka, Nature 355 (6359):430–432 (1992), the teachings of which are incorporated herein by reference.

Figure 1A:
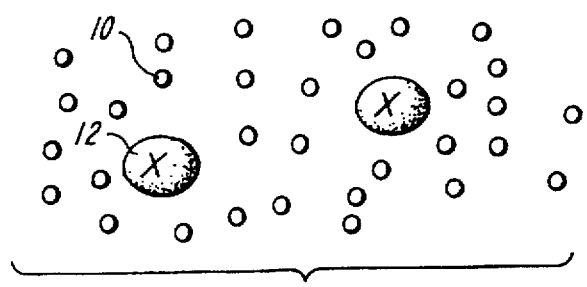
FIGS. 1A through 1D represent steps of one embodiment of a method of forming the multiple-phase transition copolymers of the invention.
Figure 1B:
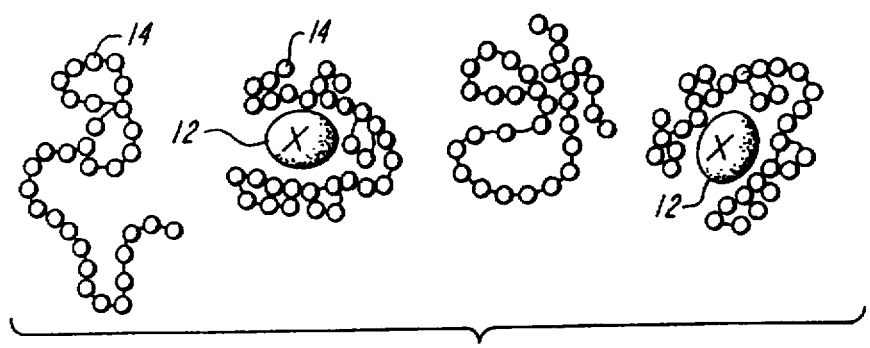

In one embodiment, the method includes forming a multiple-phase transition copolymer or gel which can selectively bind a substrate. A monomer solution is formed which, upon polymerization, will form a copolymer gel that can exhibit phase transition at a plurality of distinct phase-transition conditions. As shown in FIGS. 1A and 1B, monomer 10 of a monomer solution is combined with template 12 which, upon polymerization of monomer 10, will cause the resulting copolymer to selectively bind the substrate. Template 12, in effect, mimics the configuration of the substrate to which the resulting copolymer will selectively bind. The combined monomer solution and template 12 are exposed to conditions sufficient to cause the monomer solution to polymerize and form copolymer 14, which is shown in FIG. 1B. At least a portion of copolymer 14 forms at template 12 so that copolymer 14 is selectively configured for binding a chemical having the same or a similar chemical structure. Optionally, copolymer 14 is then ionized in an amount sufficient to cause copolymer 14 to exhibit a plurality of phase transitions upon exposure to distinct phase-transition conditions.

Figure 1C:
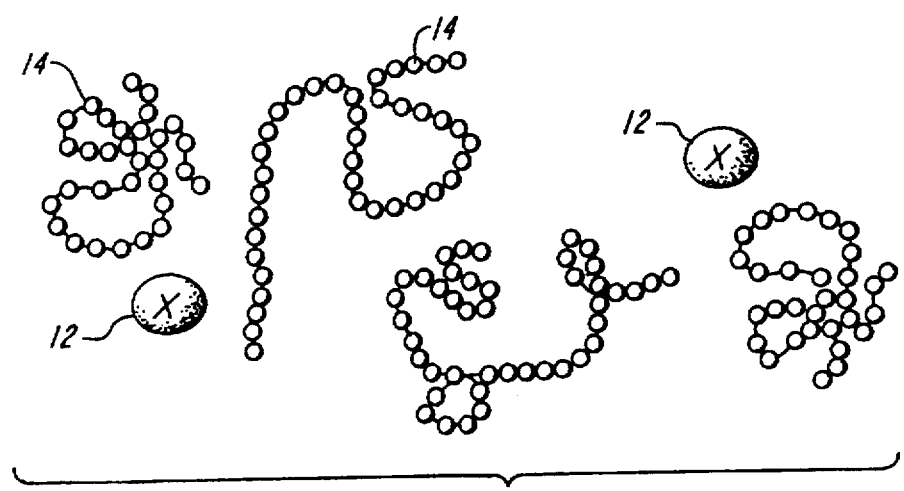
Figure 1D:
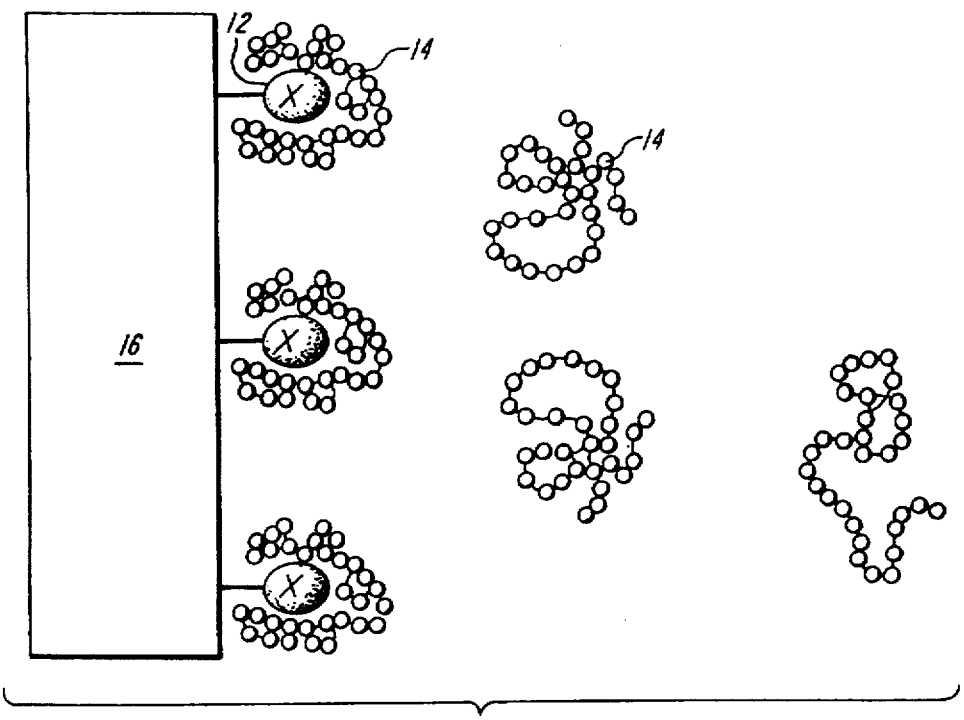

Copolymer 14 is then exposed to conditions sufficient to cause copolymer 14 to exhibit an expanding phase transition, thereby releasing template 12 from copolymer 14, as shown in FIG. 1C. Phase transition conditions at which the copolymers exhibit a discontinuous volume change can include physical conditions, chemical conditions, or combinations of physical and chemical conditions. Examples of physical phase-transition conditions include: temperature; electromagnetic radiation, such as infrared energy, visible light and ultraviolet lights; etc. Examples of chemical phase-transition conditions include: concentration of ionic species, such as hydrogen and water, i.e., pH: cross-linking agents, such as cross-linking agents which crosslink the copolymer network; inorganic and organic solvents; specific chemicals; etc. Phase-transition conditions at which copolymers exhibit a discontinuous volume change can also include combinations of physical conditions, combinations of chemical conditions, or combinations of physical and chemical conditions.

Copolymer 14 is then separated from template 12 by a suitable method, such as immersing and flushing with a large amount of water. When the copolymers are crosslinked in a form of a gel, the gel can be very easily washed. When the copolymers are not crosslinked, a dialysis bag are used to wash the copolymers.

The copolymers will then be returned to the original state by reversing the physical or chemical or combined conditions to the original condition. The copolymers will then have active sites that specifically bind the substrate.

The same procedure applies to synthesis of artificial enzymes. In this case we use as target molecules, molecules that mimic the transition state of substrate. The actual transition state of substrate is unstable. Many molecules have been recently synthesized that mimic the transition state of substrate, but stable.

Figure 2A:
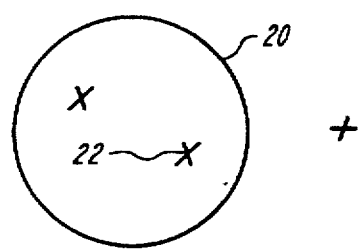
FIGS. 2A through 2F represent steps of an alternate method of forming the multiple-phase transition copolymers of the invention.
Figure 2B:
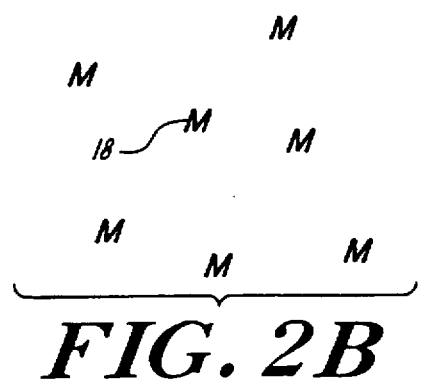
Figure 2C:
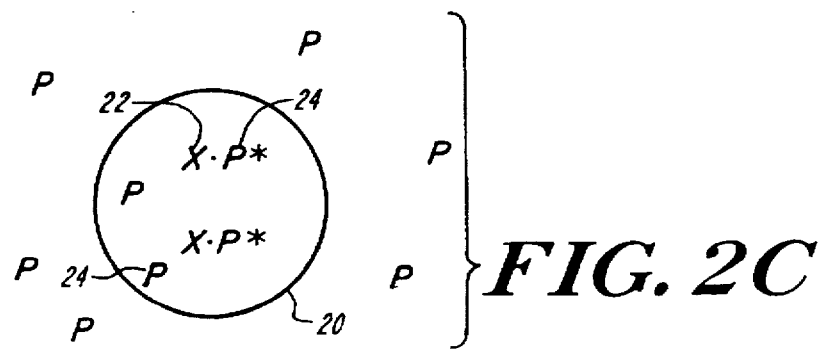

In an alternate method, shown in FIGS. 2A through 2F, monomer 18 of a monomer solution is formed which, upon polymerization, will form a copolymer that can exhibit phase transitions at a plurality of distinct phase-transition conditions. The monomer solution is combined with phase-transition gel 20 to which template 22 is bound, such as by covalent chemical bonds. The combined monomer solution and phase-transition gel 20 are exposed to conditions sufficient to cause the monomer solution to polymerize in gel 20 and form copolymer 24. A portion of the copolymer 24 forms at the template 22 and is thereby bound to phase-transition gel 20 by template 22, as shown in FIG. 2C.

Figure 2D:
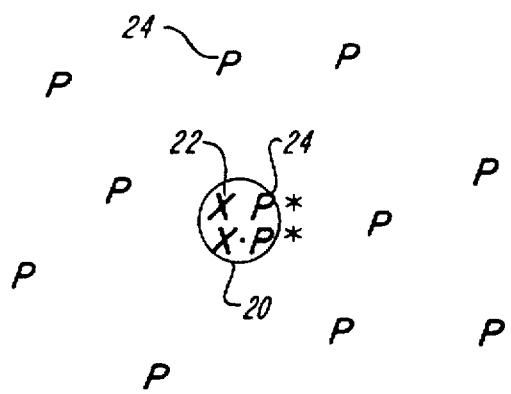
Figure 2E:
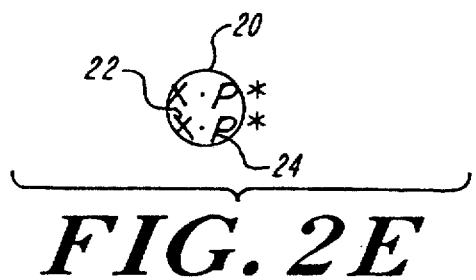
Figure 2F:

As shown in FIG. 2D, phase-transition gel 20 and copolymer 24 are then exposed to conditions sufficient to cause gel 20 to exhibit a contracting phase transition that causes copolymer 24 which is not bound to template 22 to be discharged from gel 20. Discharged copolymer 24 is then washed from gel 20. Gel 20 is subsequently exposed to conditions sufficient to cause gel 20 to exhibit an expanding phase transition and to conditions sufficient to cause copolymer 24 to exhibit a phase transition that releases copolymer 24 from template 22, as shown in FIG. 2E. Gel 20 is subsequently exposed to conditions that cause gel 20 to exhibit a contracting phase transition, whereby released copolymer 24 is discharged from gel 20, as shown in FIG. 2F.

In a particularly preferred embodiment, the phase transition gel to which the template is bound is poly(N-isopropylacrylimide). A preferred copolymer is acrylic acid/N-isopropylacrylimide/methacrylamidopropyl-ammonium-chloride (MAPTAC). In one embodiment, the monomer solution includes 440 mM of acrylic acid, 240 mM of MAPTAC, 20 mM of N-isopropylacrylimide, 0.133 grams of N,N'-methylene bisacrylamide (cross-linker), 40 mg of ammonium chloride and 100 ml of water. The monomer solution can be polymerized to form a suitable copolymer by heating the solution to about 60° C.

Examples of suitable templates include ethyl-β-fluoro-β-(p-nitrophenyl)propionate, such as is commonly used for hydrogen fluoride elimination, and p-nitrophenyl glutarate half ester, such as can be employed for ester hydrolysis.

The method for selectively binding a substrate for conversion of the substrate to a product includes combining a substrate with a copolymer, such as described above, which can bind a substrate by exposing the copolymer and the substrate to conditions which cause the copolymer to exhibit a contracting phase transition. The combined substrate and copolymer are then exposed to conditions which cause the copolymer to exhibit a first contracting phase transition, whereby the substrate is selectively bound to the copolymer. The bound substrate is then exposed to conditions which cause catalytic or enzymatic conversion of the substrate to the product. The copolymer can then be exposed to a phase-transition condition which causes the copolymer to exhibit a second contracting phase transition while the substrate is in a transition state, during the enzymatic conversion to the product.

The copolymer and the resulting product are then exposed to conditions which cause the copolymer to exhibit an expanding phase transition that releases the product.

Monomer Composition

The criterion for a proper composition is that the copolymers are prepared in one of its multiple phases. The monomers should be capable of interacting through hydrogen bonding, repulsive or attractive Coulombic interactions, hydrophobic interaction, and/or van der Waals forces. The criterion for a proper composition is that the copolymers as prepared in one of its multiple phases.

In a particularly preferred embodiment, the composition for the multiple-phase transition copolymer gel is;

| | |
|---|---|
| methacrylic acid (capable of hydrogen bonding and ionization) | 440 mM |
| dimethylacrylamide (capable of hydrogen bonding) | 240 mM |
| N-isopropylacrylamide (capable of hydrophobic interaction) | 20 mM |
| N,N'methacrylamidopropyltrimethyl-ammonium chloride (capable of electrostatic interaction) | 1 mole |
| N,N'methylene-bis-acrylamide (crosslinker) | 40 mM |
| ammonium persulfate (polymerization initiator) | 40 mg |
| water | 100 ml |

The monomer solution can be polymerized to form a suitable copolymer by heating the solution to approximately 60° C.

Examples of suitable template molecules can be rhodamine B or methylene blue, or tyrosine.

References

1. Shakhnovich, E. I. and Gutin, A. M., *Europhys. Lett.*, 8, 327–332 (1989).
2. Annaka, M. and Tanaka, T., *Nature*, 349, 400–401 (1991).
3. Tanaka, T. and Annaka, M., J. *Intelligent Material Systems and Structures*, 4, 549–552 (1993).
4. Tanaka, T., Fillmore, D. J., Sun, S.-T., Nishio, I., Swislow, G., and Shah, A., *Phys. Rev. Lett.*, 45, 1636–1639 (1980).
5. Ilmain, F., Tanaka, T., and Kokufuta, E., *Nature*, 349, 400–401 (1991).
6. Kempe, M., Fischer, L., and Mosbach, K. *Journal of Molecular Recognition*, 6, 25–29 (1991).
7. Wulff, G., *Am. Chem. Soc. Symp. Series*, 308, 186–230 (1986).

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of molecular imprinting, comprising the steps of:

providing a monomer solution that, when polymerized, is capable of undergoing at least one discontinuous phase-transition when subjected to at least one phase-transition condition;

contacting a template with the monomer solution; and exposing the template and monomer solution to conditions sufficient to polymerize the monomer, so that at least a portion of the polymerized monomer forms a copolymer gel around the template.

2. The method of claim 1, further comprising the step of causing the template to be released from the copolymer gel at a phase-transition condition.

3. The method of claim 1, wherein the step of providing a monomer solution comprises providing a monomer solution containing acrylic acid, methacrylamidopropyltrimethylammonium chloride and N-isopropylacrylamide.

4. The method of claim 1, wherein the step of providing a monomer solution comprises providing a monomer solution containing a given concentration of methacrylic acid, dimethylacrylamide, N-isopropylacrylamide, N,N'methacrylamidopropyltrimethylammonium chloride, and a given concentration of crosslinker.

5. The method of claim 1, wherein the step of contacting comprises contacting with a template selected from the group consisting of ethyl-beta-fluoro-beta-(p-nitrophenyl) propionate and p-nitrophenyl glutarate.

6. A method of molecular imprinting, comprising the steps of:

providing a monomer solution that, when polymerized, forms a copolymer gel that is capable of undergoing at least one discontinuous phase-transition when subjected to at least one phase-transition condition;

binding a template to a phase-transition polymer gel;

combining the monomer solution with the phase-transition polymer gel to which the template is bound; and polymerizing the monomer solution in the presence of the phase-transition gel to form the copolymer gel, at least a portion of the copolymer being formed around and bound to the template.

7. The method of claim 6, further comprising the step of exposing the copolymer to conditions sufficient to cause the copolymer to be released from the template and from the phase-transition gel.

8. The method of claim 6, wherein the step of providing a monomer solution comprises providing a monomer solution containing acrylic acid, methacrylamidopropylammonium chloride and N-isopropylacrylamide.

9. The method of claim 6, wherein the step of providing a monomer solution comprises providing a monomer solution containing a given concentration of methacrylic acid, dimethylacrylamide, N-isopropylacrylamide, N,N' methacrylamidopropyltrimethylammonium chloride, and a given concentration of crosslinker.

10. The method of claim 6, wherein the step of binding a template comprises binding a template selected from the group consisting of ethyl-beta-fluoro-beta-(p-nitrophenyl) propionate and p-nitrophenyl glutarate.

11. A method of molecular imprinting, comprising the steps of:

providing a monomer solution containing at least two monomers that, when polymerized, forms a copolymer gel that is capable of undergoing at least one discontinuous phase transition when subjected to at least one phase-transition condition;

contacting a template with the monomer solution; and exposing the template and the monomer solution to conditions sufficient to polymerize the monomer, so that at least a portion of the polymerized monomer forms the copolymer gel around the template.

12. The method of claim 11, wherein the step of providing comprises providing a monomer solution containing acrylic acid, methacrylamidopropyltrimethylammonium chloride and N-isopropylacrylamide.

13. The method of claim 11, wherein the step of providing comprises providing a monomer solution containing a concentration of methacrylic acid, dimethylacrylamide, N-isopropylacrylamide and N,N' methacrylamidopropyltrimethylammonium chloride and a concentration of crosslinker.

14. A composition used in molecular imprinting, comprising a copolymer capable of undergoing at least one discontinuous phase-transition when subjected to at least one phase-transition condition, the copolymer capable of specifically binding to a target molecule, at least a portion of the copolymer having been formed around the target molecule; and a template that is the target molecule or that is a structural analogue of the target molecule;

wherein the structural analogue is a molecule having a chemical structure substantially similar to the target molecule such that at least a portion of the copolymer is capable of binding to the structural analogue in a manner substantially the same as the copolymer binds to the target molecule.

15. The composition of claim 14, wherein the copolymer is derived from a monomer solution containing a concentration of methacrylic acid, dimethylacrylamide, N-isopropylacrylamide and N,N' methacrylamidopropyltrimethylammonium chloride and a crosslinker.

16. The composition of claim 14, wherein the template is selected from the group consisting of ethyl-beta-fluoro-beta-(p-nitrophenyl)propionate and p-nitrophenyl glutarate.

* * * * *